(12) United States Patent
Zhao

(10) Patent No.: US 11,391,939 B2
(45) Date of Patent: Jul. 19, 2022

(54) OPTICAL SYSTEM OF A STEREO-VIDEO ENDOSCOPE

(71) Applicant: OLYMPUS WINTER & IBE GMBH, Hamburg (DE)

(72) Inventor: Jianxin Zhao, Hamburg (DE)

(73) Assignee: OLYMPUS WINTER & IBE GMBH, Hamburg (DE)

(*) Notice: Subject to any disclaimer, the term of this patent is extended or adjusted under 35 U.S.C. 154(b) by 152 days.

(21) Appl. No.: 16/943,461

(22) Filed: Jul. 30, 2020

(65) Prior Publication Data
US 2020/0355909 A1 Nov. 12, 2020

Related U.S. Application Data

(63) Continuation of application No. PCT/EP2019/051700, filed on Jan. 24, 2019.

(30) Foreign Application Priority Data

Feb. 1, 2018 (DE) .......................... 102018102268.9

(51) Int. Cl.
*G02B 23/00* (2006.01)
*G02B 23/24* (2006.01)
*G02B 27/00* (2006.01)

(52) U.S. Cl.
CPC ..... *G02B 23/2415* (2013.01); *G02B 23/2423* (2013.01); *G02B 23/2453* (2013.01); *G02B 27/0018* (2013.01)

(58) Field of Classification Search
CPC ............ G02B 23/2415; G02B 23/2423; G02B 23/2453; G02B 27/0018; G02B 23/2407; G02B 21/00; G02B 21/0004; G02B 21/18; G02B 21/20; G02B 21/22; G02B 21/36; G02B 21/361; A61B 1/00; A61B 1/00064; A61B 1/00066; A61B 1/00071;
(Continued)

(56) References Cited

U.S. PATENT DOCUMENTS 5,689,365 A 11/1997 Takahashi
10,088,665 B2 10/2018 Zhao et al.
(Continued)

FOREIGN PATENT DOCUMENTS

DE 102013215422 A1 2/2015
DE 102014206513 A1 10/2015
(Continued)

OTHER PUBLICATIONS

International Search Report dated May 9, 2019 issued in PCT/EP2019/051700.

*Primary Examiner* — Arnel C Lavarias
(74) *Attorney, Agent, or Firm* — Scully, Scott, Murphy & Presser, P.C.

(57) ABSTRACT

An optical system of a stereo-video endoscope with a sideways viewing direction, the optical system including: a sideways-viewing distal optical assembly; and a proximal optical assembly; wherein the distal optical assembly includes an inlet lens, a deflecting unit configured as a prism unit, and an outlet lens on a common optical axis one after the other in the direction of light incidence, the proximal optical assembly includes a left and a right lens system channel, the lens system channels being identically configured and arranged parallel to each other, each lens system channel having its own optical axis, and the outlet lens is formed with one or more of a light-impermeable coating on a light inlet side facing the deflecting unit and with a light-impermeable coating formed on a light outlet side facing away from the deflecting unit in a central region of the outlet lens.

9 Claims, 3 Drawing Sheets

(58) Field of Classification Search
CPC .......... A61B 1/00096; A61B 1/00098; A61B 1/00163; A61B 1/00174; A61B 1/00177; A61B 1/00186; A61B 1/00193; A61B 1/04; A61B 1/043; A61B 1/0646
USPC ....... 359/419, 362, 363, 368, 369, 372, 373, 359/374, 375, 376, 377, 378, 384, 423, 359/434, 435; 600/101, 109, 111, 129, 600/130, 160, 162, 166, 170, 171, 175, 600/176, 177, 181
See application file for complete search history.

(56) References Cited

U.S. PATENT DOCUMENTS

| | | | | |
|---|---|---|---|---|
| 2002/0161278 | A1* | 10/2002 | Nakamura | G02B 23/243 600/111 |
| 2009/0296235 | A1 | 12/2009 | Igarashi | |
| 2016/0370580 | A1 | 12/2016 | Takada et al. | |
| 2017/0235121 | A1 | 8/2017 | Igarashi | |
| 2018/0003944 | A1 | 1/2018 | Fujii | |

FOREIGN PATENT DOCUMENTS

| | | | | |
|---|---|---|---|---|
| EP | 1542053 B1 * | 11/2007 | ......... | A61B 1/00193 |
| JP | 8-82766 A | 3/1996 | | |
| JP | 2009-288682 A | 12/2009 | | |
| JP | 2016-527566 A | 9/2016 | | |
| WO | 2015/133431 A1 | 9/2015 | | |
| WO | WO 2015/150078 A1 | 10/2015 | | |
| WO | WO-2017104427 A1 * | 6/2017 | ......... | A61B 1/00096 |
| WO | WO 2017/104427 A1 | 10/2018 | | |

\* cited by examiner

Prior Art

OPTICAL SYSTEM OF A STEREO-VIDEO ENDOSCOPE

CROSS-REFERENCE TO RELATED APPLICATION

The present application is a continuation of PCT/EP2019/051700 filed on Jan. 24, 2019, which is based upon and claims the benefit to DE 10 2018 102 268.9 filed on Feb. 1, 2018, the entire contents of each of which are incorporated herein by reference.

BACKGROUND

Field

The present disclosure relates to an optical system for use with an endoscope and more particularly to an optical system of a stereo-video endoscope with a sideways viewing direction, comprising a sideways-viewing distal optical assembly and a proximal optical assembly, wherein the distal optical assembly comprises an inlet lens, a deflecting unit designed as a prism unit, and an outlet lens on a common optical axis one after the other in the direction of light incidence, and the proximal optical assembly comprises a left and a right lens system channel, wherein the lens system channels are identically designed and are arranged parallel to each other, and each lens system channel has its own optical axis.

The present disclosure additionally relates to a stereo-video endoscope with a sideways, in particular fixed, viewing direction as well as the use of a lens for an optical system of a stereo-video endoscope.

Prior Art

Video endoscopes, in which the light entering at a distal tip of an endoscope shaft is diverted by an optical system onto one or more image sensors, are known in various embodiments. There are endoscopes which look forward and have a so-called 0° viewing direction, endoscopes with a (fixed) sideways viewing direction as well as endoscopes with an adjustable viewing direction (also referred to as VDOV endoscopes).

In addition, stereo-video endoscopes are known, which are designed to acquire a stereoscopic pair of images and/or two stereoscopic video channels. With such instruments, it is possible to produce a 3D image of an object located distally before the end of the endoscope shaft in an examination or operating space.

Stereo-video endoscopes with a sideways viewing direction are sideways-viewing endoscopes having a fixed viewing angle which deviates from the forward view. Such endoscopes frequently comprise a prism arrangement made of multiple prisms which reflect the beams of light entering the optical system from the object space at an angle to the longitudinal axis of the endoscope shaft twice and deflect them in an unreversed way in the direction of the endoscope shaft. Such an endoscope is known, for example, from DE 10 2014 206 513 A1 owned by Olympus Winter & Ibe GmbH, Hamburg.

A deflection prism arrangement of such a stereo-video endoscope typically comprises two or three prisms. The prisms are frequently cemented to one another at their common interfaces. In the case of such a deflection prism arrangement, the incident light bundles are reflected off two reflecting interfaces of a second or third prism, which are located diagonally both to the optical axis of the inlet lens and to the longitudinal axis of the endoscope shaft. The second or third prism of the deflection prism arrangement is situated in the direction of light incidence behind a first or second prism which is arranged behind the inlet lens. The diagonal reflecting interface of the second or third prism, at which the second reflection takes place, partially forms a common interface with the front prism which the incident beams of light pass through first.

The inlet lens of the optical system of such a stereo-video endoscope defines the optical axis of the optical system. The optical system comprises diaphragms or menisci which specify a field of view or respectively the aperture angle of the optics. Within the field of view, light bundles incident in the optical system are imaged by the optical system on one or more image sensors. Light bundles, which are incident in the optical system from outside of the field of view or as a result of multiple reflections, thus produce so-called "ghost images" or "flares".

A known deflection prism assembly, in which such ghost images can occur, comprises a first prism and a second prism which are cemented to one another. The first prism has an inlet side and an outlet side, wherein the inlet side is inclined with respect to the outlet side. The outlet side of the first prism immediately adjoins a second inlet side of the second prism. For example, the first and the second prisms are cemented to one another on these two sides. The second prism additionally comprises a reflection side and a second outlet side. Light, which is incident in the deflection prism assembly from the field of view, traverses the inlet side of the first prism and exits again at the outlet side thereof. The light subsequently travels directly through the second inlet side into the second prism, is reflected off the reflection side within the second prism and leaves the latter at the outlet side.

FIG. 2 shows a simplified schematic sectional view of an optical system, as is known for example from DE 10 2013 215 422 A1 owned by Olympus Winter & Ibe GmbH, Hamburg. The optical system comprises a sideways-viewing distal optical assembly 16 which is arranged behind an inlet window 10. For example, the depicted optical system can be located in a distal portion of a stereo-video endoscope. In addition to the distal optical assembly 16, the optical system comprises a proximal optical assembly 18. This can be rotated, for example, by rotating a rotating wheel in the endoscope shaft.

The distal optical assembly 16 comprises an inlet lens 20 which is, for example, formed as a raised negative meniscus. It comprises a convex outer surface 22 and a concave inner surface 24. The light entering from the left side through the inspection window 10 traverses the inlet lens 20 and enters a deflecting unit 26 configured as a prism unit. The deflecting unit comprises two prisms having a partially mirrored or respectively mirrored interface. The light incident diagonally from the side is deflected by the deflecting unit 26 in the direction of a longitudinal axis of the endoscope shaft. The deflecting unit 26 comprises a first partially mirrored prism 28 which comprises the partially mirrored interface 26b. Additionally, the deflecting unit 26 comprises a further partially mirrored prism 30, which is not depicted in greater detail, and the mirrored interface 26a.

The distal optical assembly 16 additionally comprises an outlet lens 32 which is arranged in the direction of light incidence behind a diaphragm 34. Alternatively, no diaphragm is provided between the outlet lens 32 and the deflecting unit 26. In this case, diaphragms are arranged in each case in the direction of light incidence before the rod lenses 40L, 40R of the proximal optical assemblies 18 for a left lens system channel 38L and a right lens system channel 38R.

The light originating from the deflecting unit 26 enters the outlet lens 32. The outlet lens 32 is, by way of example, formed as a hollow positive meniscus lens. It has a concave inlet surface 36a and a convex outlet surface 36b. The curvature radius of the concave inlet surface 36a is greater than the curvature radius of the convex outlet surface 36b.

After a short distance, the light exiting from the outlet lens 32 reaches the proximal optical assembly 18. The latter comprises a left lens system channel 38L and a right lens system channel 38R. The two lens system channels 38L, 38R are identically configured and are arranged parallel to each other. The left optical channel has a left optical axis LoA and the right optical channel has a right optical axis RoA. The optical axes LoA, RoA are oriented at least approximately parallel to each other. The two lens system channels 38L, 38R each comprise a rod lens 40L, 40R, which the light originating from the outlet lens 32 of the distal optical assembly 16 first enters. A group of achromatic lenses 42L, 42R is in each case joined to the left and right rod lens 40L, 40R in the direction of light incidence. The groups of achromatic lenses 42L, 42R are each formed as triplets. The light is deflected by these onto the left or respectively right image sensor 44L, 44R, such that the examination or operating space located before the distal tip of the endoscope shaft is imaged stereoscopically.

Further details regarding the design of the optical system shown in FIG. 2 are to be inferred from the indicated DE 10 2013 215 422 A1.

SUMMARY

Thus, it is an object to prevent the production of ghost images in a simple way in a stereo-video endoscope.

Such object can be achieved by an optical system of a stereo-video endoscope with a sideways viewing direction, comprising a sideways-viewing distal optical assembly and a proximal optical assembly, wherein the distal optical assembly comprises an inlet lens, a deflecting unit designed as a prism unit, and an outlet lens on a common optical axis one after the other in the direction of light incidence, and the proximal optical assembly comprises a left and a right lens system channel, wherein the lens system channels are identically designed and are arranged parallel to each other, and each lens system channel has its own optical axis, and the outlet lens is formed with a light-impermeable coating on the light inlet side facing the deflecting unit and/or with a light-impermeable coating on the light outlet side facing away from the deflecting unit in the central region of the outlet lens.

The outlet lens of the distal optical assembly, which can be arranged on the prism unit of the distal optical assembly, is provided with a coating, as a result of which no light penetrates the central region through the outlet lens and the production of ghost images in the lens system channels is minimized or prevented.

The outlet lens can be formed as a prism lens, wherein the beams of light for the left and right optical channel are allowed to pass between the region of the light-permeable coating on the outlet lens and the outer edge of the outlet lens. In the central region of the outlet lens, in which the coating or coatings are applied to the outlet lens, no beams of light are allowed to pass. Thanks to the coating or coatings, the outlet lens has an optical passage region in the form of a ring or in the manner of a ring.

The coating on the outlet lens can be formed in the form of a circle or in the manner of a circle.

The outlet lens for the left lens system channel and the right lens system channel of the proximal optical assembly can be permeable to light, wherein the optical passage region of the outlet lens can be formed in the form of a ring or in the manner of a ring outside of the coating(s).

The side of the outlet lens facing away from the deflecting unit can be convex.

The outlet lens can be formed as a concave-convex lens.

Moreover, the coating on the outlet lens can be formed as an anti-reflex coating. Such coating can be provided as an anti-reflex coating, in order to reduce or avoid the creation of flares or ghost images.

The light-impermeable coating or the anti-reflex coating can be formed as a chromium coating.

In addition, such object can be achieved by a stereo-video endoscope having a fixed, for example, sideways, viewing direction having an optical system as described above. The optical system can comprise one or more of the previously indicated embodiments.

Moreover, such object can be achieved by the use of a lens for an optical system of a stereo-video endoscope having a fixed viewing direction, wherein the optical system can be formed according to the embodiments indicated above, wherein the lens is formed as an outlet lens of a distal optical assembly and is formed with a light-impermeable coating on the light inlet side facing a deflecting unit of the distal optical assembly and/or with a light-impermeable coating on the light outlet side facing away from a deflecting unit of the distal optical assembly in the central region of the outlet lens.

Further features will become evident from the description of embodiments, together with the claims and the appended drawings. Embodiments can fulfill individual features or a combination of multiple features.

BRIEF DESCRIPTION OF THE DRAWINGS

The embodiments are described below without limiting the general concept of the invention by means of exemplary embodiments with reference to the drawings, wherein reference is expressly made to the drawings regarding all of the details which are not explained in greater detail in the text, wherein.

In the drawings, the same or similar elements and/or parts are, in each case, provided with the same reference numerals so that they are not introduced again in each case.

DETAILED DESCRIPTION

Figure 1:
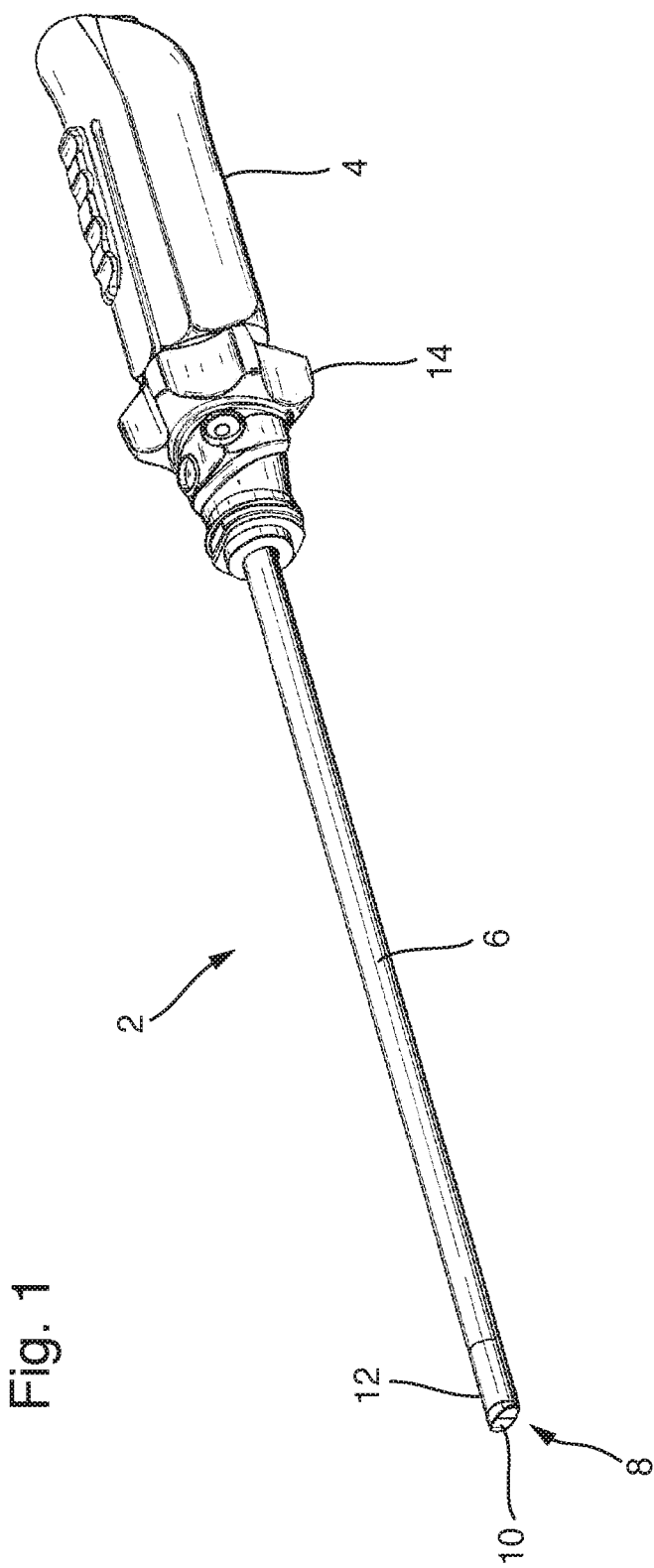
FIG. 1 schematically illustrates a stereo-video endoscope in a simplified perspective representation.

FIG. 1 shows a simplified perspective representation of an endoscope 2 having a proximal handle 4 and a rigid endoscope shaft 6. An inspection window 10 is located at a distal tip 8 of the endoscope shaft 6. A distal portion 12 of the endoscope shaft 6 is joined thereto. An optical system, which is not visible in FIG. 1, is arranged in the distal portion 12, with which optical system an examination or operating field located before the distal tip 8 of the endoscope 2 is imaged on image sensors which are likewise not depicted. A rotating wheel 14, with which the optical system located in the interior of the endoscope shaft 6 can be turned azimuthally, is joined to the handle 4 in the distal direction.

Figure 2:
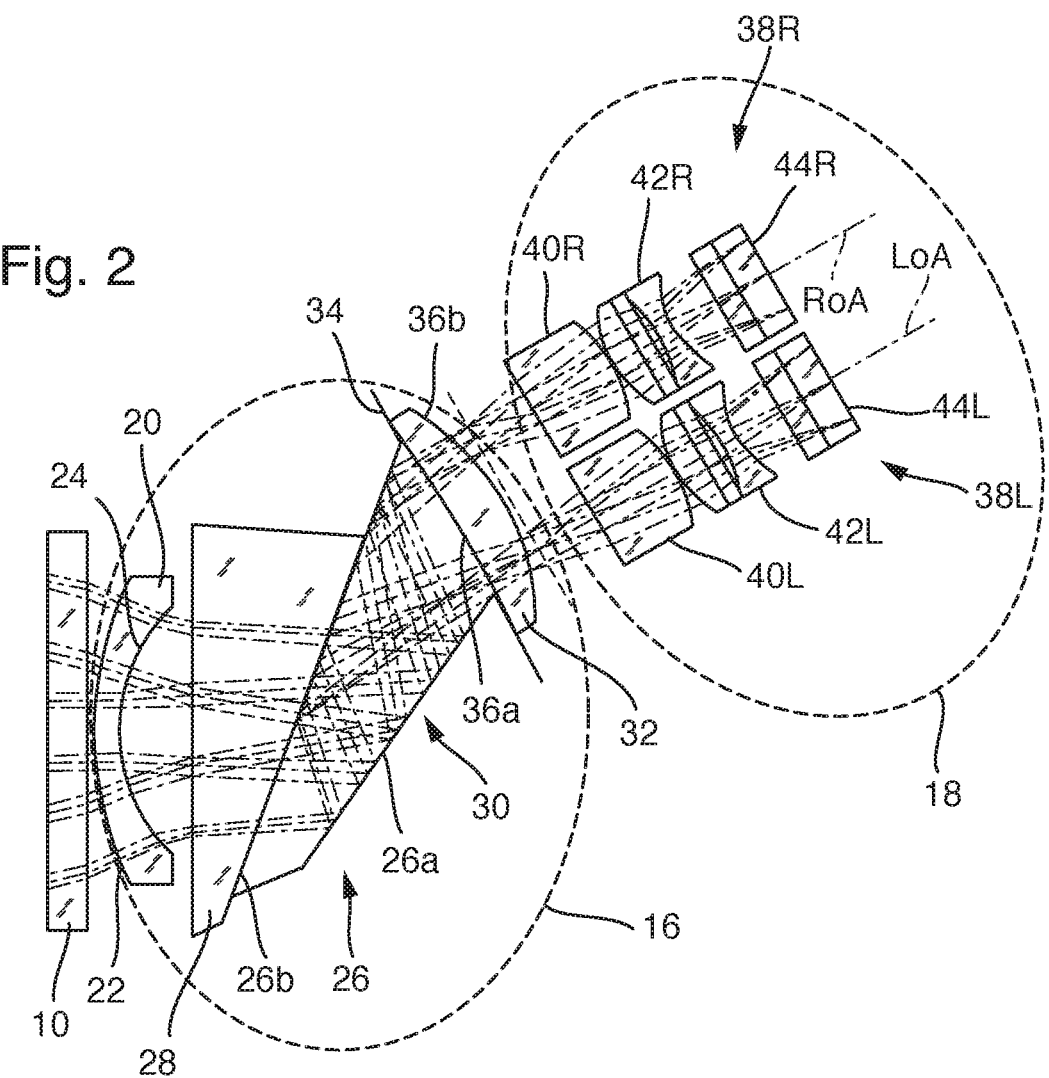
FIG. 2 illustrates an optical system of a stereo-video endoscope according to the prior art in a simplified schematic sectional view, FIG. 3a schematically illustrates a cross-section through an outlet lens of a distal optical assembly of the stereo-video endoscope, and FIG. 3b schematically according to the invention a view of the outlet lens of the distal optical assembly.
Figures 3A, 3B:
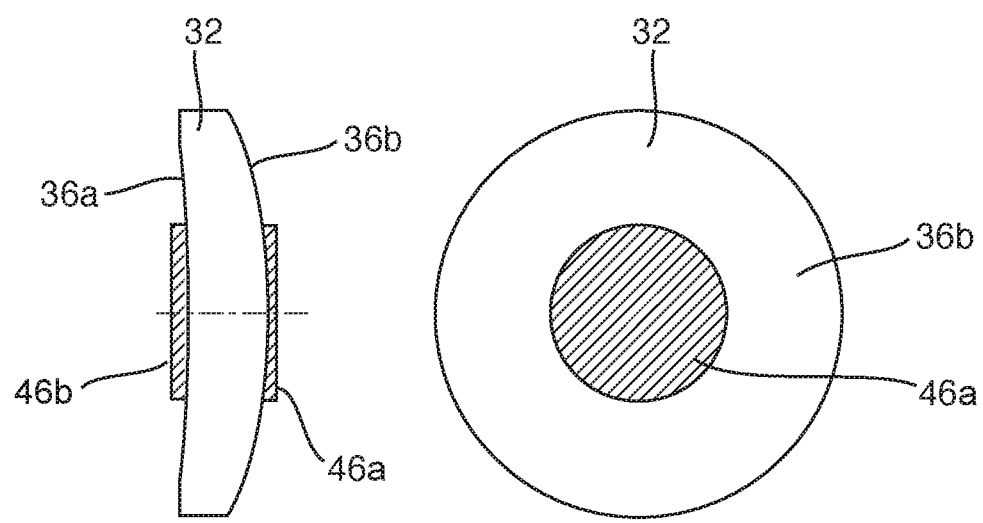

In FIGS. 3a and 3b, a cross-sectional view (FIG. 3a) and a front view (FIG. 3b) of an outlet lens 32 of the distal optical module 16 (cf. FIG. 2) according to an embodiment are schematically depicted. In this case, the outlet lens 32 is formed as a concave-convex lens having a concave inlet surface 36a and a convex outlet surface 36b.

An outlet side coating 46a in the form of a circle is formed on the convex outlet surface 36b in the central region such that, in the region of the coating 46a, no light is allowed to pass by the coating 46a in the central region. Similarly, a coating 46b in the form of a circle is formed on the concave inlet surface 36a in the central region such that, in the region of the coating 46b, no light is allowed to pass by the coating 46b in the central region. Although the outlet lens 32 is shown in FIG. 3a having coatings 46a, 46b formed on each of the inlet and outlet surfaces 36a, 36b, the outlet lens 32 can only have the coating 46a on the outlet surface 36b or only have the coating 46b on the inlet surface 36a. The coatings 46a and/or 46b can be formed as a circular surface on the respective inlet and outlet surfaces. The coatings 46a and/or 46b can be formed as a chromium coating. An optical system of the embodiment of FIGS. 3a and 3b is configured similarly to that of the optical system of FIG. 2 with the exception that the outlet lens of FIG. 2 is replaced with the outlet lens 32 of FIGS. 3a and 3b having one or both of the coatings 46a and 46b.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

2 Stereo-video endoscope
4 Handle
6 Endoscope shaft
8 Distal tip
10 Inspection window
12 Distal portion
14 Rotating wheel
16 Distal optical assembly
18 Proximal optical assembly
20 Inlet lens
22 Outer surface
24 Inner surface
26 Deflecting unit
26a, 26b Interface
28 Partially mirrored prism
30 Further partially mirrored prism
32 Outlet lens
34 Diaphragm
36a Concave inlet surface
36b Convex outlet surface
38L Left lens system channel
38R Right lens system channel
40L, 40R Rod lens
42L, 42R Achromatic lens group
44L, 44R Image sensor
46a Outlet Side Coating
46b Inlet Side Coating
LoA Left optical axis
RoA Right optical axis

The invention claimed is:

1. An optical system of a stereo-video endoscope with a sideways viewing direction, the optical system comprising:
a sideways-viewing distal optical assembly; and
a proximal optical assembly;
wherein the distal optical assembly comprises an inlet lens, a deflecting unit configured as a prism unit, and an outlet lens on a common optical axis one after the other in a direction of light incidence,
the proximal optical assembly comprises a left and a right lens system channel, the lens system channels being identically configured and arranged parallel to each other, each lens system channel having its own optical axis, and
the outlet lens is formed with one or more of a light-impermeable coating on a light inlet side facing the deflecting unit and with a light-impermeable coating formed on a light outlet side facing away from the deflecting unit in a central region of the outlet lens.

2. The optical system according to claim 1, wherein the coating formed on the outlet lens is formed in a form of a circle.

3. The optical system according to claim 1, wherein the outlet lens is permeable to light.

4. The optical system according to claim 1, wherein the light outlet side of the outlet lens is convex.

5. The optical system according to claim 1, wherein the outlet lens is formed as a concave-convex lens.

6. The optical system according to claim 1, wherein the coating on the outlet lens is formed as an anti-reflex coating.

7. The optical system according to claim 6, wherein the anti-reflex coating is formed as a chromium coating.

8. A stereo-video endoscope having a fixed viewing direction, the stereo-video endoscope comprising the optical system according to claim 1.

9. A method of forming an optical system for use in a stereo-video endoscope having a fixed viewing direction, the method comprising:
assembling a sideways-viewing distal optical assembly; and
assembling a proximal optical assembly;
wherein the distal optical assembly comprises an inlet lens, a deflecting unit configured as a prism unit, and an outlet lens on a common optical axis one after the other in a direction of light incidence,
the proximal optical assembly comprises a left and a right lens system channel, the lens system channels being identically configured and arranged parallel to each other, each lens system channel having its own optical axis, and
the assembly of the distal optical assembly comprises forming the outlet lens with one or more of a light-impermeable coating on a light inlet side facing the deflecting unit and with a light-impermeable coating on a light outlet side facing away from the deflecting unit in a central region of the outlet lens.

* * * * *